(12) United States Patent
Kullik et al.

(10) Patent No.: US 6,745,767 B2
(45) Date of Patent: Jun. 8, 2004

(54) RESPIRATION SYSTEM WITH AN ELECTRICALLY DRIVEN ROTARY COMPRESSOR

(75) Inventors: Götz Kullik, Lübeck (DE); Hans-Ullrich Hansmann, Barnitz (DE); Andreas Krause, Lübeck (DE)

(73) Assignee: Dräger Medizintechnik GmbH, Lübeck (DE)

( * ) Notice: Subject to any disclaimer, the term of this patent is extended or adjusted under 35 U.S.C. 154(b) by 163 days.

(21) Appl. No.: 09/823,794

(22) Filed: Mar. 30, 2001

(65) Prior Publication Data
US 2002/0002974 A1 Jan. 10, 2002

(30) Foreign Application Priority Data
Jul. 6, 2000 (DE) .......................................... 100 32 913

(51) Int. Cl.[7] ................................................ F16K 1/08
(52) U.S. Cl. ............................ 128/204.19; 128/204.21; 416/3; 417/17

(58) Field of Search ..................... 128/200.24, 203.12, 128/200.14–200.23, 204.18, 205.24, 207.14–207.18; 416/3, 30, 31, 35, 44; 417/15, 18, 22, 42, 48, 50, 61, 322, 17

(56) References Cited

U.S. PATENT DOCUMENTS

| | | | | |
|---|---|---|---|---|
| 4,944,748 A | * | 7/1990 | Bramm et al. ............... 417/356 |
| 5,470,208 A | * | 11/1995 | Kletschka ................... 417/356 |
| 5,856,719 A | * | 1/1999 | De Armas ................... 310/103 |
| 5,875,783 A | * | 3/1999 | Kullik ..................... 128/204.18 |
| 6,302,105 B1 | * | 10/2001 | Wickham et al. ......... 128/204.18 |

* cited by examiner

Primary Examiner—Glenn K. Dawson
(74) Attorney, Agent, or Firm—McGlew and Tuttle, P.C.

(57) ABSTRACT

A respiration system is provided with an electrically driven rotary compressor as a gas delivery unit. The system makes a low-noise mounting of the gas delivery wheel possible. The gas delivery wheel can also be washed and sterilized and ensures a reliable separation of the breathing gas from the electric components. The respiration system rotary compressor is mounted magnetically axially and radially during operation.

21 Claims, 3 Drawing Sheets

RESPIRATION SYSTEM WITH AN ELECTRICALLY DRIVEN ROTARY COMPRESSOR

FIELD OF THE INVENTION;

The present invention pertains to a respiration system with an electrically driven rotary compressor as described, e.g., in U.S. Pat. No. 5,875,783.

BACKGROUND OF THE INVENTION

Such respiration systems are used especially in the area of medicine and especially in anesthesia apparatus where expensive anesthetics are usually used and recirculation of the exhaled gases and the new added fresh gases is therefore especially desirable. The use of rotary compressors as a gas delivery unit in respiration systems is highly advantageous because correspondingly dimensioned rotary compressors are particularly suitable for rapidly following the spontaneous breathing of a patient by changing the speed of rotation. One drawback of the prior-art rotary compressors in respiration systems is the mechanical mount, which cannot be washed and sterilized. In addition, the bearing lubricant necessary for the mechanical rolling bearings becomes unfit for use during the necessary cleaning. Another drawback of the prior art mechanical mount arises from the noise emissions generated, especially at high speeds of rotation.

Furthermore, a separation between the electric components of the respiration system or the gas delivery unit and the breathing gas is necessary even in open respiration systems without rebreathing because the breathing gas has, in general, an increased oxygen concentration and there is therefore a risk of fire without separation in the case of damage to the insulation.

SUMMARY AND OBJECTS OF THE INVENTION

The object of the present invention is to provide a respiration system which makes possible a low-noise mounting of a gas delivery unit, which unit can also be washed and sterilized and which unit ensures a reliable separation of the breathing gas from the electric components.

One essential advantage of the present invention arises from the fact that the rotary compressor acting as the gas delivery unit is mounted floatingly by means of magnetic interactions and is driven electrically, more specifically electromagnetically in a contactless manner. The service life is practically unlimited due to the floating mount.

In addition, the solution according to the present invention makes it possible to remove, clean, sterilize and reinstall the components swept by the breathing gas so that the respiration system can be used reliably, with low noise, hygienically and conveniently even in recirculation operation.

The special design of the drive according to the present invention includes a magnetically mounted rotary compressor with a can and a stationary seal between the rotary compressor and the stationary components of the mount and the drive.

This can seal must be able to be fluxed magnetically. The seal may generate only weak eddy currents and should be manufactured from a material (ceramic, plastic) which provides a good sliding pairing together with the surface of the rotary compressor. This sliding interaction makes possible the deceleration of the rotary compressor without too much friction and heating in the case of an emergency caused by the failure of the magnetic bearing.

The seal comprises a thin can, which is located on the inner side of the stator and is smooth-walled and preferably cylindrical. This can, which is also called a "slit tube seal" in other areas of engineering, is cyclically fluxed by the driving magnetic field; the mechanical components do not perform any relative movements. The seal is not subject to wear and its service life is not limited, either.

In principle, various combinations of active magnetic bearings with electrically energized coils with position sensors and passive magnetic bearings with permanent magnets are possible. It should be noted in this connection that not all six possible degrees of freedom of the rotary compressor with passive magnetic bearings can be floated with permanent magnets. At least one degree of freedom must be actively energized and operated in a position-controlled manner, i.e., there always is at least one active magnetic bearing with electrically energized coils.

It is especially advantageous to design the radial bearings as actively energized and position-controlled magnetic bearings. With this, it is possible to allow the rotary compressor to rotate at high speeds of rotation around its principal axis of inertia rather than around its geometric axis of rotation and thus not to generate any vibrations caused by imbalance.

This imbalance compensation is achieved by taking into account measured values of the position and current. The energization of the active electromagnets, which is variable over time, is performed by means of the measured values.

The stiffness and the damping of the magnetic bearing can thus be influenced, so that a so-called free run is achieved. The controlled parameters of the magnetic bearing control circuit can be adaptively changed as a function of the speed of rotation in a characteristic diagram.

The energization of the active magnetic bearing is favorably switched on and operated before the drive. The rotary compressor floats when stopped and will then be driven floatingly.

Only the position of the rotor is controlled at low speeds of rotation; the state of imbalance is calculated at higher speeds of rotation from the power consumption of the individual radial bearing coils and compensated such that the rotor will no longer rotate around its geometric axis of rotation but around its principal axis of inertia.

The system may use an electric drive of any design that does not require any mechanical contact between the stator and the rotor. A three-phase asynchronous motor with cage rotor or the brushless, electronically commuted d.c. motor with permanent magnet rotor are suitable for use as the electric drive.

In the brushless, electronically commuted d.c. motor, the rotor of the drive is a diametrically magnetized permanent magnet, and the stator of the drive comprises especially three drive coil pairs, which are arranged at an angle of 120° in relation to one another such that the field vector of the drive coil magnetic field can be rotated around the axis of the rotor. The position of the rotor permanent magnet is recognized either by means of Hall sensors or, during the rotation, by voltages induced in the drive coils. The individual drive coils are then energized consecutively cyclically such that the rotor rotates. This cyclic energization as a function of the position of the rotor (commutation) takes place without wear by means of semiconductor circuit components.

The magnetic bearing is especially advantageous with respect to the noises which originate to a great extent from the rolling bearings of the gas delivery means in prior-art respirators and anesthesia apparatuses and then disappear completely.

In principle, any rotary compressor, especially radial compressors, but also side-channel compressors or peripheral compressors may be used for gas delivery.

The simple design of the components swept by the gas makes it possible to remove, clean, sterilize and reinstall these components in the field. This allows for the use of a closed respiration system.

There is hermetic separation between the breathing gas with increased oxygen concentration and the current-carrying electric components.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
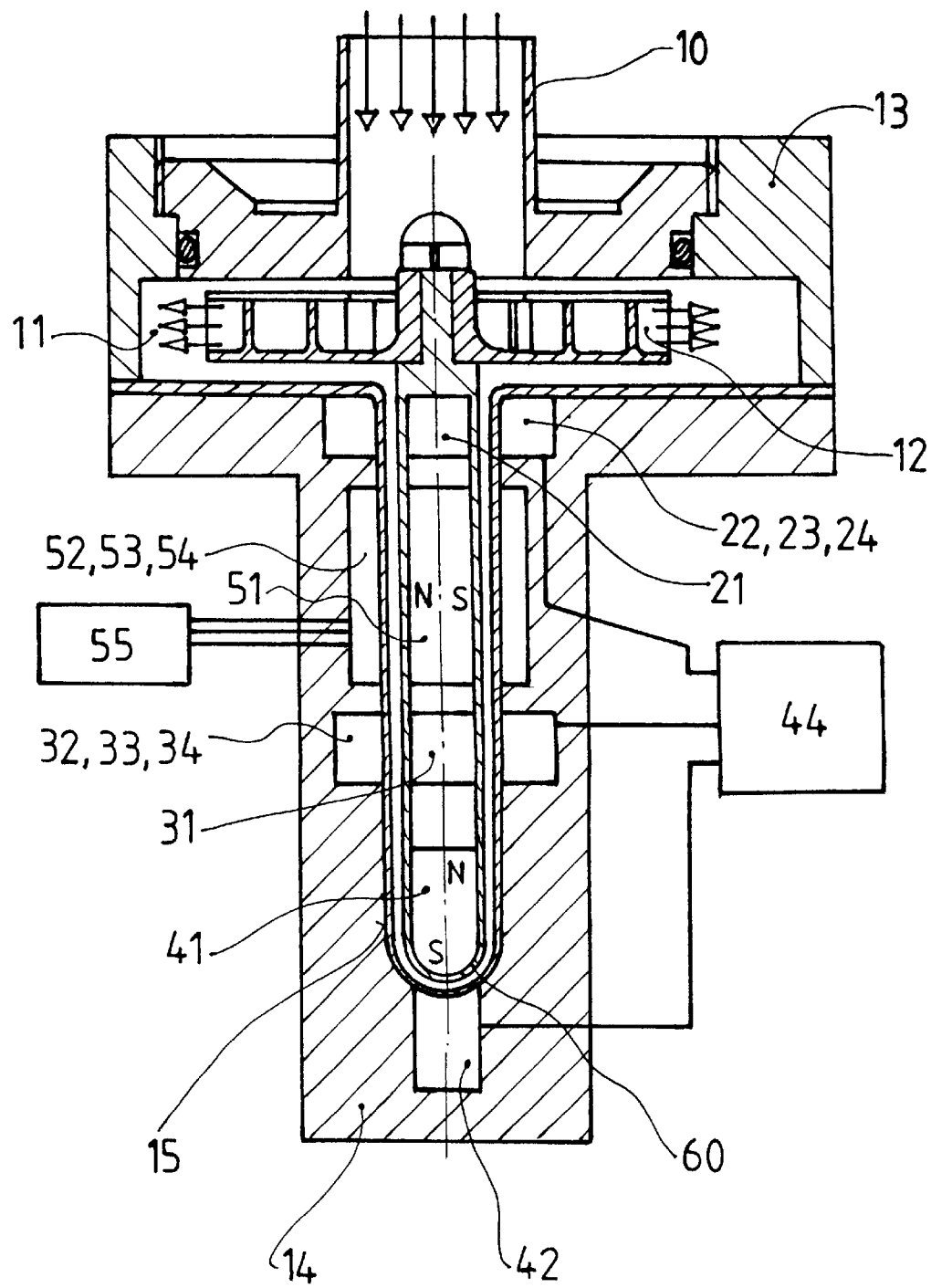
FIG. 1 is a sectional view through a gas delivery unit of a respiration system according to the present invention.

Referring to the drawings in particular, in the exemplary embodiment according to FIG. 1, the gas delivery unit of the respiration system is designed as a rotary compressor and especially as a radial compressor. The radial compressor 110 has a gas-carrying housing 13 with an intake (low pressure) fitting 10 and a pressure (discharge) fitting 11. The radial compressor also has a basic body 14 with stationary bearing and drive elements, a gap pot, slit pot or can seal 15 and a compressor wheel 12 with rotating bearing elements and drive elements. A rotary compressor equipped only with active magnetic bearings and brushless, electronically commuted d.c. drive is shown in the exemplary embodiment according to FIG. 1.

The two radial bearings comprise two soft magnetic rotor components 21 and 31, three stationary coils 22, 23, 24 and 32, 33, 34 each as well as position sensors, (shown schematically at 22, 23, 24 and 32, 33, 34). The thrust bearing comprises a rotating first permanent magnet 41 and a stationary coil with iron core 42 as well as a position sensor. All coils and the position sensors, are supplied and energized by a common evaluating and control unit 44.

The drive comprises a rotating, diametrically magnetized rotor permanent magnet 51 and three stationary drive coil pairs 52, 53, 54, which are arranged at an angle of 120° in relation to one another such that the field vector of the drive coil magnetic field can be rotated around the axis of the rotor. The position of the rotor permanent magnet 51 is provided either by means of Hall sensors or, during the rotation, by voltages induced in the drive coils. The individual drive coil pairs 52, 53, 54 are energized by a drive electronic unit 55 cyclically one after another such that the rotor rotates. This cyclic energization as a function of the position of the rotor (commutation) takes place without wear by means of semiconductor circuit components of the evaluating and control unit 44.

All rotor elements of the compressor wheel 12 are encapsulated in a jacket tube 60, and the entire rotor can be simply removed for cleaning and sterilization. The (gap pot, slit pot or) can seal 15 can also be removed and processed, and the basic body 14 with the current-carrying components is hermetically separated from the patient gas and from the gas with increased oxygen concentration.

For operation, the active magnetic bearings (21 to 24, 31 to 34 and 41, 42) are first actuated, so that the rotor or the compressor wheel 12 floats without rotating, and the drive is then activated. Only the position of the rotor is controlled at low speeds of rotation. The state of imbalance is also calculated at higher speeds of rotation from the power consumption of the individual radial bearing coils and compensated such that the rotor no longer rotates around its geometric axis of rotation but around its principal axis of inertia. Slim rotors rotate around their smallest principal axis of inertia. Since the rotation around the smallest principal axis of inertia is not stable in the case of energy dissipation due to friction, the compensation is of great significance. Nutating vibrations develop without imbalance compensation; these are actively damped by the compensation.

Interfering forces are generated in all rotating systems due to deviations from true running and tolerances of the position sensors and bearing coils. Active magnetic bearings make it possible to make such periodic interfering forces disappear. The imbalance forces are calculated, e.g., from the measured current values during position-controlled operation and a component in antiphase is thus additionally superimposed to the bearing coil currents. A rotor controlled in this manner rotates freely around its principal axis of inertia; all acting forces are at equilibrium and no periodic force is transmitted to the housing.

Figure 2:
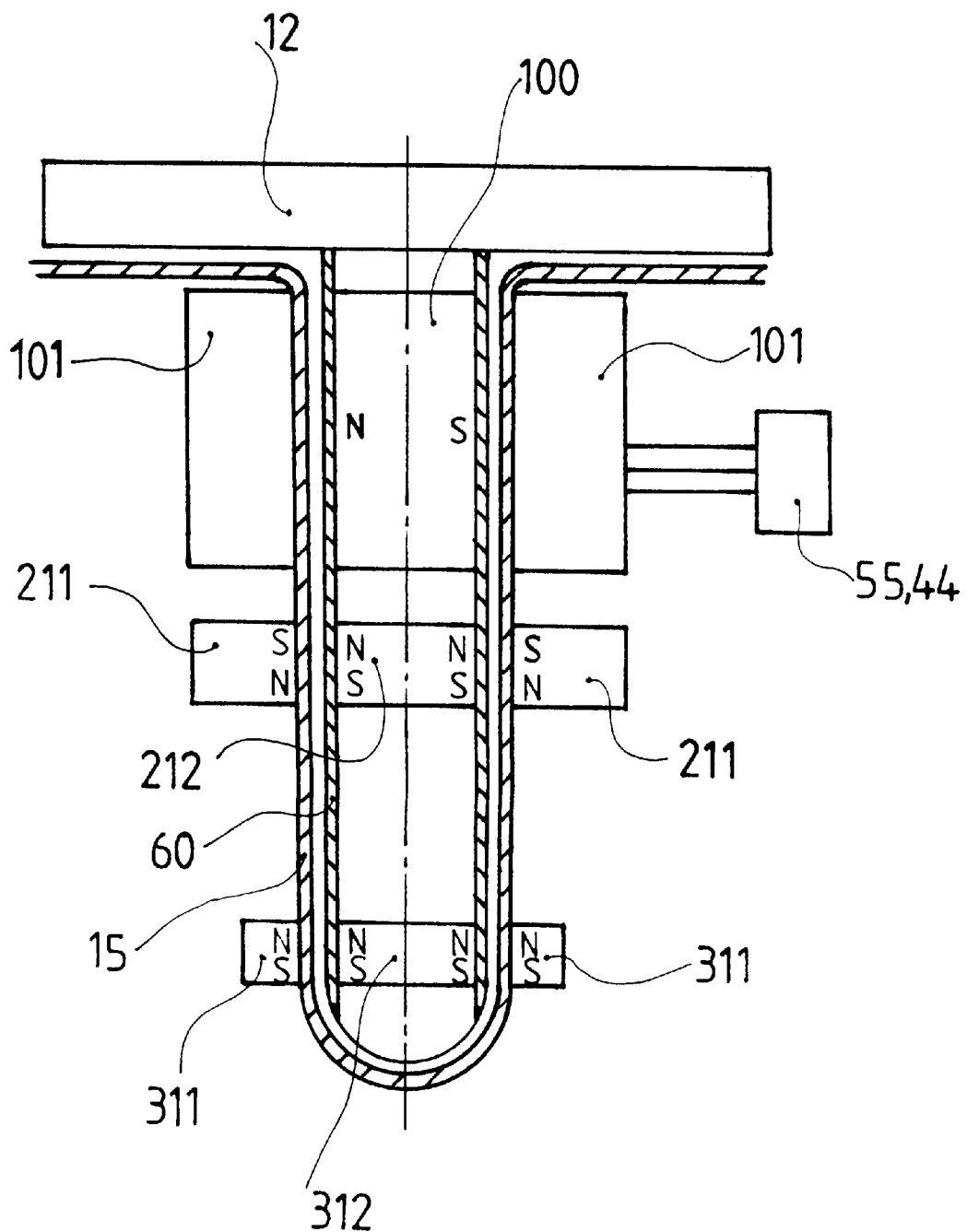
FIG. 2 is a sectional view through a gas delivery unit of a second respiration system according to the present invention.

FIG. 2 shows an example of a rotary compressor with a combination of active and passive magnetic fields. A first, active radial bearing with a first radial bearing magnet 100 belonging to it is operated actively. The bearing coils 101 belonging to the radial bearing are located in the drive and utilize the central bundle of laminations as a magnetic short-circuit. This combination is called a "bearingless motor" and it makes possible a very inexpensive design. The second, passive radial ball bearing with third permanent magnets 311, 312 is based on repulsion and is arranged at a great distance from the first, active radial bearing. The destabilizing effect of this second radial bearing, which effect is always present in passive bearings, is compensated by a powerful passive thrust bearing with second permanent magnets 211, 212. The destabilizing effect of this thrust bearing is compensated by the active first radial ball bearing in the "bearingless motor." The amount of materials and electronics needed in this exemplary embodiment is minimized, but no imbalance compensation is possible because position sensors are only present in the "bearingless motor" 100, 101.

Figure 3:
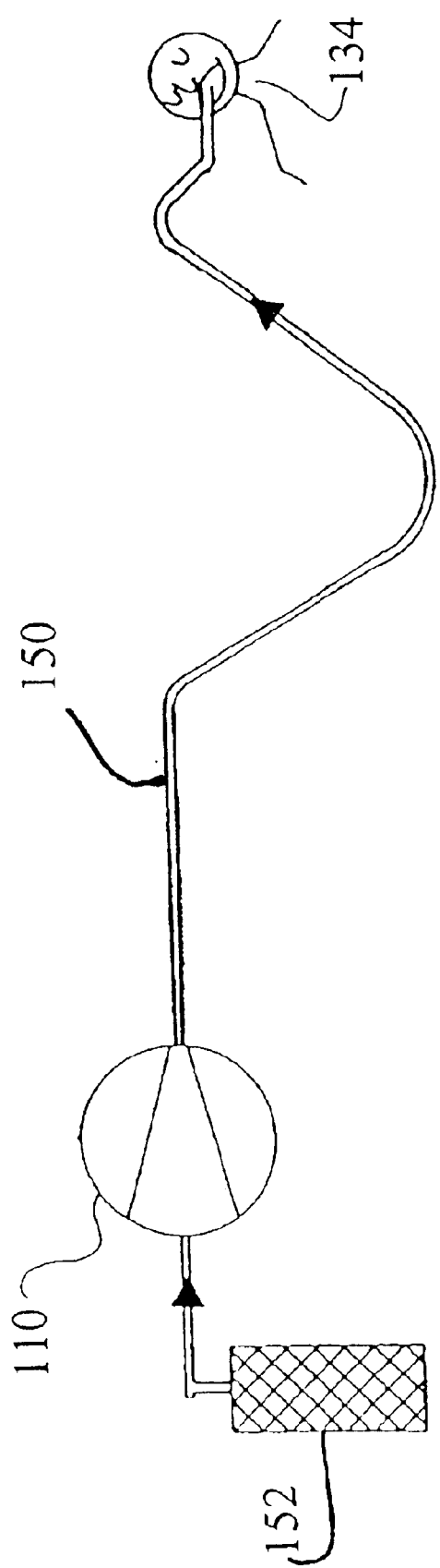
FIG. 3 is a diagram showing an anesthetic dispenser and a gas flow line connected to the compressor of the invention.

FIG. 3 shows an anesthesia apparatus. During inhalation, the radial flow compressor 110 with the drive motor draws in a mixture of anesthetic from the anesthetic device 152 and sends it to a gas flow line 150.

What is claimed is:

1. A respiration system, comprising:

an electrically driven rotary compressor gas delivery unit with a housing, a compressor wheel with an axial magnetic bearing element, a radial magnetic bearing element and a rotary drive element, a rotary drive associated with said housing and cooperating with said rotary drive element, an axial magnetic bearing associated with said housing and cooperating with said axial magnetic bearing element, and a radial magnetic bearing associated with said housing and cooperating with said radial magnetic beating element, said axial magnetic bearing and said radial magnetic bearing supporting said compressor wheel axially and radially during rotation of said compressor for operation, wherein said axial magnetic bearing and said radial magnetic bearing are each active magnetic bearings with electrically energized coils; and a control and evaluating unit receiving signals corresponding to speed of rotation of said compressor wheel and power consumption of the individual active magnetic bearings and calculating the state of imbalance of said compressor wheel from the measured speeds of rotation of said compressor wheel and the necessary power consumption of the individual active magnetic bearings and compensating by controlling compressor mounting support such that said compressor wheel will no longer rotate around its geometric axis of rotation but around a principal axis of inertia of said compressor wheel.

2. A respiration system in accordance with claim 1, wherein said rotary compressor gas delivery unit is a radial compressor, a side-channel compressor or a peripheral compressor.

3. A respiration system in accordance with claim 1, wherein said rotary compressor gas delivery unit is part of an anesthesia apparatus with an anesthetic dispensing device.

4. A respiration system in accordance with claim 1, further comprising a smooth-walled cylindrical can seal arranged between said compressor wheel and stationary components of the magnetic bearings, said axial magnetic bearing element, said radial magnetic bearing element and said rotary drive element being provided in a shaft portion of said compressor wheel enclosed in a jacket tube to seal said axial magnetic bearing element, said radial magnetic bearing element and said rotary drive element with respect to an exterior of said shaft portion.

5. A respiration system in accordance with claim 1, wherein said control and evaluating unit varies coil current to said radial magnetic bearing element until the compressor wheel rotates around a compressor wheel principal axis of inertia by superimposing to the coil currents a component of measured current values during position-controlled operation, the component of the measured current values being a superimposed in antiphase to the coil currents.

6. A respiration system comprising:
a gas flow line;
a gas delivery housing with a chamber with an intake opening and with a discharge opening, said gas flow line being to said housing in flow connection with said discharge opening;
a gas delivery wheel with a shaft portion extending in an axial direction and a wheel portion extending in a radial direction, the shaft portion having, a gas delivery wheel radial magnetic bearing part, a gas delivery wheel motor part and a gas delivery wheel axial magnetic bearing part at a shaft portion lower end, said axial direction being substantially vertical and said radial direction being substantially horizontal;
an axial magnetic bearing element supported by said housing at a location adjacent to said chanter, said axial magnetic bearing element being positioned below said shaft portion to interact with said gas delivery wheel axial magnetic bearing part;
a radial magnetic bearing element supported by said housing at a location adjacent to said cavity, said radial magnetic bearing element being positioned to interact with said gas delivery wheel radial magnetic bearing part;
magnetic motor coils supported by said housing at a location adjacent to said cavity, positioned to interact with said gas delivery wheel motor part; and
a drive electronic unit connected to said magnetic motor coils for energizing said magnetic motor cods for rotation of said gas delivery wheel for operation and for providing power to said axial magnetic bearing element and said radial magnetic bearing element such that said gas delivery wheel is positioned in a vertical position and in a horizontal position in said cavity.

7. A respiration system in accordance with claim 6, further comprising:
a control unit for providing power to said axial magnetic bearing element and said radial magnetic bearing element such that said gas delivery wheel is in a floating position in said chamber.

8. A respiration system in accordance with claim 7, wherein said axial magnetic bearing element and said radial magnetic bearing element are each active magnetic bearings with electrically energized coils.

9. A respiration system in accordance with claim 6, wherein one of said axial magnetic bearing element and said radial magnetic bearing element is an active magnetic bearing with electrically energized bearing coils and at least one of said axial magnetic bearing element and said radial magnetic bearing element is a passive magnetic bearing with permanent magnets.

10. A respiration system in accordance with claim 6, wherein said radial magnetic bearing element is an active radial magnetic bearing with electrically energized bearing coils and further comprising a passive radial magnetic bearing with permanent magnets only and at least one passive axial magnetic bearing with permanent magnets only.

11. A respiration system in accordance with claim 6, further comprising a control and evaluating unit receiving signals corresponding to a speed of rotation of the gas delivery wheel and power consumption of the individual magnetic elements and calculating the state of imbalance of the gas delivery wheel from the measured speeds of rotation of the gas delivery wheel and the necessary power consumption of the individual active magnetic bearings and compensating by controlling gas delivery wheel mounting support such that the gas delivery wheel will no longer rotate around its geometric axis of rotation but around its principal axis of inertia.

12. A respiration system in accordance with claim 11, wherein said control and evaluating unit varies coil current to said radial magnetic bearing element until the gas delivery wheel rotates around a gas delivery wheel principal axis of inertia by superimposing to the coil currents a component of measured current values during position-controlled operation, the component of the measured current values being superimposed in antiphase to the coil currents.

13. A respiration system in accordance with claim 6, wherein the gas delivery wheel is a radial compressor, a side-channel compressor or a peripheral compressor.

14. A respiration system in accordance with claim 6, wherein the gas delivery wheel is part of an anesthesia apparatus with an anesthetic dispensing device.

15. A respiration system in accordance with claim 6, further comprising a smooth-walled cylindrical can seal arranged between said gas delivery wheel and said housing, covering said axial magnetic bearing element, said radial magnetic bearing element and said magnetic motor coils, said axial magnetic bearing element, said radial magnetic bearing element and said rotary drive element being provided in said shaft portion of said gas delivery wheel enclosed in a jacket tube to seal said axial magnetic bearing element, said radial magnetic bearing element and said rotary drive element with respect to an exterior of said shaft portion.

16. A respiration system, comprising:

a gas flow line;

a gas delivery housing with a cavity with an intake opening and a discharge opening, said gas flow line being connected to said housing in flow connection with said discharge opening;

a gas delivery wheel with an shaft portion extending in an axial direction and a wheel portion extending in a radial direction, the shaft portion having a gas delivery wheel axial magnetic bearing part at a lower end of said shaft portion, a gas delivery wheel radial magnetic bearing part and a gas delivery wheel motor part, said axial direction being substantially vertical and said radial direction being substantially horizontal;

a vertical magnetic bearing element supported by said housing at a location adjacent to said cavity and below said shaft portion, said vertical magnetic bearing element being positioned to interact with said gas delivery wheel axial magnetic bearing part to provide a magnetic force acting on said gas delivery wheel in a vertical direction relative to said housing;

a horizontal magnetic bearing element supported by said housing at a location adjacent to said cavity, said horizontal magnetic, bearing element being positioned to interact with said gas delivery wheel radial magnetic bearing part to provide a magnetic force acting on said gas delivery wheel in a horizontal direction relative to said housing;

magnetic motor coils supported by said housing at a location adjacent to said cavity, positioned to interact with said gas delivery wheel motor pan; and a drive electronic unit connected to said magnetic motor coils for energizing said magnetic motor coils for rotation of said gas delivery wheel for operation and for providing power to said vertical magnetic bearing element and said horizontal magnetic bearing element such that said gas delivery wheel is positioned in a vertical position and a horizontal position in said cavity, said vertical magnetic bearing and said horizontal magnetic bearing each being active magnetic bearings with electrically energized coils with feedback signals sent to said drive electronic unit to control the horizontal and vertical disposition of said gas delivery wheel in said cavity.

17. A respiration system in accordance with claim 16, wherein said drive electronic unit is a control and evaluating unit receiving signals corresponding to speed of rotation of the gas delivery wheel and power consumption of the individual magnetic bearing elements and calculating the state of imbalance of the gas delivery wheel from the measured speeds of rotation of the gas delivery wheel and the necessary power consumption of the individual active magnetic bearings and compensating a power signal to said horizontal magnetic bearing element until the gas delivery wheel rotates around a gas delivery wheel principal axis of inertia.

18. A respiration system in accordance with claim 17, wherein said control and evaluating unit varies coil current to said horizontal magnetic bearing element until the gas delivery wheel rotates around a gas delivery wheel principal axis of inertia by superimposing to the coil currents a component of measured current values during position-controlled operation, the component of the measured current values being superimposed in antiphase to the coil currents.

19. A respiration system in accordance with claim 16, wherein the gas delivery wheel is a radial compressor, a side-channel compressor or a peripheral compressor.

20. A respiration system in accordance with claim 16, wherein the gas delivery wheel is part of an anesthesia apparatus with an anesthetic dispensing device.

21. A respiration system in accordance with claim 16, further comprising a smooth-walled cylindrical can seal arranged between said gas delivery wheel and said housing, covering said vertical magnetic bearing element, said horizontal magnetic bearing element and said magnetic motor coils, said axial magnetic bearing element, said radial magnetic bearing element and said rotary drive element being provided in said shaft portion of said gas delivery wheel enclosed in a jacket rube to seal said axial in magnetic bearing element, said radial magnetic bearing element and said rotary drive element with respect to an exterior of said shaft portion.

* * * * *